(12) United States Patent
Tkaczyk et al.

(10) Patent No.: US 7,583,779 B2
(45) Date of Patent: Sep. 1, 2009

(54) SYSTEM AND METHOD FOR ACQUISITION AND RECONSTRUCTION OF CONTRAST-ENHANCED, ARTIFACT-REDUCED CT IMAGES

(75) Inventors: J. Eric Tkaczyk, Delanson, NY (US); Deborah Walter, Burnt Hills, NY (US); Yanfeng Du, Rexford, NY (US)

(73) Assignee: General Electric Company, Schenectady, NY (US)

( * ) Notice: Subject to any disclaimer, the term of this patent is extended or adjusted under 35 U.S.C. 154(b) by 647 days.

(21) Appl. No.: 10/904,716

(22) Filed: Nov. 24, 2004

(65) Prior Publication Data

US 2006/0109949 A1    May 25, 2006

(51) Int. Cl.
*A61B 6/00* (2006.01)
(52) U.S. Cl. .............................. 378/4; 378/5
(58) Field of Classification Search ............... 378/4–21, 378/901
See application file for complete search history.

(56) References Cited

U.S. PATENT DOCUMENTS

| | | | | |
|---|---|---|---|---|
| 3,950,613 A | * | 4/1976 | Macovski | 378/2 |
| 3,965,358 A | * | 6/1976 | Macovski | 378/5 |
| 4,029,963 A | * | 6/1977 | Alvarez et al. | 378/5 |
| 4,464,775 A | * | 8/1984 | Yamagishi | 378/5 |
| 4,482,918 A | * | 11/1984 | Keyes et al. | 378/98.11 |
| 4,603,428 A | * | 7/1986 | Sandrik et al. | 378/174 |
| 4,686,695 A | * | 8/1987 | Macovski | 378/146 |
| 4,789,930 A | * | 12/1988 | Sones et al. | 378/207 |
| 4,856,528 A | * | 8/1989 | Yang et al. | 382/131 |
| 5,400,378 A | | 3/1995 | Toth | |
| 5,490,218 A | * | 2/1996 | Krug et al. | 382/100 |
| 5,729,582 A | * | 3/1998 | Ham et al. | 378/89 |
| 5,943,388 A | * | 8/1999 | Tumer | 378/98.9 |
| 6,018,562 A | * | 1/2000 | Willson | 378/9 |
| 6,345,113 B1 | * | 2/2002 | Crawford et al. | 382/131 |
| 6,399,951 B1 | * | 6/2002 | Paulus et al. | 250/370.13 |

(Continued)

OTHER PUBLICATIONS

Cahn et al., Detective quantum efficiency dependence on x-ray energy weighting in mammography, Med Phys, 26 (12), Dec. 1999, pp. 2680-2683.*

(Continued)

*Primary Examiner*—Edward J Glick
*Assistant Examiner*—Alexander H Taningco
(74) *Attorney, Agent, or Firm*—Ziolkowski Patent Solutions Group, SC

(57) ABSTRACT

A system and method are disclosed for reconstructing contrast-enhanced CT images that are substantially free of beam-hardening artifacts. An imaging system includes a radiation source configured to project radiation toward an object to be scanned and an energy discriminating detector assembly having a plurality of detector elements and configured to detect radiation emitted by the radiation source and attenuated by the object to be scanned. The imaging system also includes computer programmed to count a number of photons detected by each detector element and associate an energy value to each counted photon and determine a material composition of a CT view from the number of photons counted and the energy value associated with each counted photon. The computer is also programmed to apply a weighting to the CT view based on the material composition of the CT view and reconstruct an image with differential weighting based on the weighting of the CT view.

60 Claims, 12 Drawing Sheets

U.S. PATENT DOCUMENTS

| | | | | |
|---|---|---|---|---|
| 6,529,575 | B1* | 3/2003 | Hsieh | 378/4 |
| 6,614,874 | B2* | 9/2003 | Avinash | 378/62 |
| 6,658,081 | B2* | 12/2003 | Bruder et al. | 378/15 |
| 6,683,933 | B2* | 1/2004 | Saito et al. | 378/4 |
| 6,683,934 | B1* | 1/2004 | Zhao et al. | 378/9 |
| 6,819,738 | B2* | 11/2004 | Hoffman | 378/19 |
| 6,999,549 | B2* | 2/2006 | Sabol et al. | 378/5 |
| 7,298,812 | B2* | 11/2007 | Tkaczyk et al. | 378/5 |
| 2002/0097320 | A1 | 7/2002 | Zalis | 348/65 |
| 2003/0012331 | A1* | 1/2003 | Kojima et al. | 378/4 |
| 2003/0023163 | A1 | 1/2003 | Johnson et al. | 600/431 |
| 2003/0113267 | A1 | 6/2003 | Knopp et al. | 424/19.363 |
| 2004/0092814 | A1* | 5/2004 | Hsieh et al. | 600/425 |
| 2004/0101088 | A1* | 5/2004 | Sabol et al. | 378/4 |
| 2004/0101104 | A1* | 5/2004 | Avinash et al. | 378/98.12 |
| 2004/0136491 | A1 | 7/2004 | Iatrou et al. | 378/4 |
| 2004/0264626 | A1* | 12/2004 | Besson | 378/4 |
| 2004/0264627 | A1 | 12/2004 | Besson | |
| 2005/0084069 | A1* | 4/2005 | Du et al. | 378/98.9 |
| 2005/0220265 | A1* | 10/2005 | Besson | 378/16 |

OTHER PUBLICATIONS

Niederlohner et al., Practical Aspects of Energy Weighting in X-ray Imaging, IEEE, 2004, pp. 3191-3194.*

Niederlohner et al., The energy weighting technique: measurements and simulations, Nuclear Instruments and Methods in Physics Research A, 546, 2005, pp. 37-41.*

F. Rashid-Farrokhi et al., Local Tomography in Fan-Beam Geometry Using Wavelets, IEEE, 1996, 0-7803-3258-X/96, pp. 709-712.

* cited by examiner

SYSTEM AND METHOD FOR ACQUISITION AND RECONSTRUCTION OF CONTRAST-ENHANCED, ARTIFACT-REDUCED CT IMAGES

BACKGROUND OF THE INVENTION

The present invention relates generally to radiographic imaging and, more particularly, to a system and method for acquisition and reconstruction of contrast-enhanced and artifact-reduced CT images. The present invention further relates to system and method for processing CT data to increase contrast-to-noise ratio (CNR) and reduce artifacts in the reconstructed image.

Typically, in radiographic systems, an x-ray source emits x-rays toward a subject or object, such as a patient or a piece of luggage. Hereinafter, the terms "subject" and "object" may be interchangeably used to describe anything capable of being imaged. The x-ray beam, after being attenuated by the subject, impinges upon an array of radiation detectors. The intensity of the radiation beam received at the detector array is typically dependent upon the attenuation of the x-rays through the scanned object. Each detector of the detector array produces a separate signal indicative of the attenuated beam received by each detector. The signals are transmitted to a data processing system for analysis, further processing and, ultimately, image reconstruction.

In a similar fashion, radiation detectors are employed in emission imaging systems such as used in nuclear medicine (NM) gamma cameras and Positron Emission Tomography (PET) systems. In these systems, the source of radiation is no longer an x-ray source, rather it is a radiopharmaceutical introduced into the body being examined. In these systems each detector of the array produces a signal in relation to the localized intensity of the radiopharmaceutical concentration in the object. Similar to conventional x-ray imaging, the strength of the emission signal is also attenuated by the interlying body parts. Each detector element of the detector array produces a separate signal indicative of the emitted beam received by each detector element. The signals are transmitted to a data processing system for processing, analysis, and image reconstruction.

In most computed tomography (CT) imaging systems, the x-ray source and the detector array are rotated about a gantry encompassing an imaging volume around the subject. X-ray sources typically include x-ray tubes, which emit the x-rays as a fan or cone beam from the anode focal point. X-ray detector assemblies typically include a collimator for reducing scattered x-ray photons from reaching the detector, a scintillator adjacent to the collimator for converting x-rays to light energy, and a photodiode adjacent to the scintillator for receiving the light energy and producing electrical signals therefrom. Typically, each scintillator of a scintillator array converts x-rays to light energy. Each photodiode detects the light energy and generates a corresponding electrical signal. The outputs of the photodiodes are then transmitted to the data acquisition system and then to the processing system for image reconstruction.

Conventional CT imaging systems utilize detectors that convert x-ray photon energy into current signals that are integrated over a time period, then measured and ultimately digitized. A drawback of such detectors is their inability to provide independent data or feedback as to the energy and incident flux rate of photons detected. That is, conventional CT detectors have a scintillator component and photodiode component wherein the scintillator component illuminates upon reception of x-ray photons and the photodiode detects illumination of the scintillator component and provides an integrated electrical current signal as a function of the intensity and energy of incident x-ray photons. While it is generally recognized that CT imaging would not be a viable diagnostic imaging tool without the advancements achieved with conventional CT detector design, a drawback of these integrating detectors is their inability to provide energy discriminatory data or otherwise count the number and/or measure the energy of photons actually received by a given detector element. Accordingly, recent detector developments have included the design of an energy discriminating detector that can provide photon counting and/or energy discriminating feedback. In this regard, the detector can be caused to operate in an x-ray counting mode, an energy measurement mode of each x-ray event, or both. That is, such energy discriminating detectors are capable of not only x-ray counting but also providing a measurement of the energy level of each x-ray detected.

In x-ray projection systems and CT imaging modalities that do not utilize energy discrimination, the contrast between target objects and background objects is formed by differences in x-ray attenuation between target and background materials. In this case, larger differences in x-ray attenuation translate to improved differentiation of the target materials from the background materials. However, typically, images contain multiple materials and mixtures of materials that may yield similar contrasts in an x-ray projection or reconstructed CT image and make differentiation of the target objects difficult.

In systems utilizing energy integrating detectors, the detector signal is formed as a specific weighted sum of x-ray events. The specific weighting function for an energy integrating detector is proportional to the energy for each x-ray photon. Therefore, the high energy x-rays are weighted more heavily than the low energy x-rays. The nature of the detector dictates the this specific weighting function. As a result, information available in the x-ray data and from the a priori knowledge of anatomy is not typically considered, which may lead to sub-optimal weighting.

In systems utilizing energy discriminating detectors, it is possible to differentiate materials within the subject of the imaging. As such, some methods have been proposed to apply a generalized weight factor which is some specific function of the x-ray energy to improve the detective quantum efficiency (DQE) in specific applications, such as mammography applications. However, such generalized x-ray energy weighting functions include limitations when actually implemented because they are globally implementated for all pixels in an image and do not specifically take into account the energy-dependent, x-ray attenuation properties of each tissue locally. For example, these general x-ray energy weighting functions which may be optimized for enhancing high atomic materials such as bone and iodine contrast agents will result in reduced CNR when imaging soft tissue materials having low atomic numbers. Furthermore, performance degradation is incurred due to the limited number of energy bins used during data acquisition and due to detector electronic noise. Accordingly, when such generalized x-ray energy weighted acquisitions are performed instead of equally weighted acquisitions, increased noise is experienced in the reconstructed image.

Another drawback of generalized x-ray energy weighted approaches is that low energy photons are heavily weighted, which increases noise within a reconstructed image. That is, typically, low energy photons can not penetrate the imaging subject effectively and, thus, the majority of low energy photons are attributable to noise. Accordingly, when a generalized x-ray energy weighted approach is applied and low energy photons are heavily weighted, noise, which comprises a large percentage of the low energy photons, is increased within the reconstructed image.

Additionally, conventional CT imaging can create a visualization of the density of the tissue and substances imaged in the subject. The density is derived as related to x-ray attenuation of the tissue and is encoded as a grey scale value in order to form an image. Density information is often used to segment regions of the images and associate those regions with certain biological tissues. For example, high attenuation is often associated with bone. By performing segmentation based on density information, it is possible to remove bone from the image so as to generate a soft-tissue-only image.

In addition, the technique of dual energy material discrimination uses the value of attenuation acquired at two or more energies to differentiate tissues. This dual energy technique creates two individual images that projects the energy sensitive response of each tissue onto that of two "basis" materials. The result of this technique is a set of two images, each of which is a projection onto a single basis vector. Since the energy dependence of attenuation is related to atomic number, additional atomic-number-related information is displayed which is different and complimentary to the grayscale density map. This technique of data analysis and dual energy projection image formation differentiates tissues and allows new diagnostic interpretations by physicians or medical specialists. However, it requires the viewing of multiple images during evaluation and diagnosis.

When utilizing systems employing energy discriminating detectors, additional information is available from such energy selective detector systems that can be used to produce information related to the atomic number of tissues without extrapolating the atomic number information from the density of the tissue. However, this additional information is not typically utilized during the display of medical images.

Conventional CT images represent the x-ray attenuation of an object under investigation. The CT number for a given pixel within the image is determined by a linear attenuation coefficient for that pixel averaged over the x-ray spectrum. Beam hardening errors occur because the energy spectrum is different at different locations across the volume of the object. As a result, conventional CT does not provide quantitative image values. Beam-hardening errors are often present in conventional CT images because a given material may be located at different locations that are at varying distances from the x-ray source and, therefore, the given material provides differing contributions to the x-ray projection.

Due to the polychromatic x-ray beam spectrum and energy dependent attenuation coefficients, the x-ray attenuation and the path length is generally non-linear. This non-linear relationship can cause beam-hardening artifacts such as non-uniformity, shading, and streaking. These image artifacts can lead to misdiagnosis and limit the usefulness to perform quantitative analysis on CT images.

Since more than 80% of a human body is water, beam hardening artifacts can be at least partially corrected by remapping the projection data based on the x-ray beam spectrum and water attenuation characteristics. However, when the scanned object is highly heterogeneous and its attenuation characteristics deviate significantly from those of water, the water beam hardening correction become inadequate. For example, in a head scan, where there is a large amount of bony structure present in addition to the soft tissues, water beam hardening correction is an insufficient compensation technique. Accordingly, residual errors and image artifacts are present after water beam hardening correction is applied and dark banding between dense objects and degraded bone-brain interface may be found in the reconstructed image.

To combat these artifacts, some approaches have been proposed. However, these approaches rely on an assumed average bone thickness and density or on iteratively estimated bone contents in the water corrected image. As such, should the actual bone structure deviate even slightly from the assumed or estimated the bone structure, over-correction or under-correction errors may cause less than optimal imaging results.

It would therefore be desirable to design a method and system capable of reconstructing an image with reduced beam hardening artifacts and with increased material differentiation to aid in distinguishing various materials within an image. It would also be desirable to have a system and method capable of reconstructing an image that is substantially free of beam-hardening artifacts and with material variations clearly distinguished or identified.

BRIEF DESCRIPTION OF THE INVENTION

The present invention is directed to a method and apparatus for CT data acquisition and processing that overcomes the aforementioned drawbacks. A CT system is configured to reconstruct a beam-hardening-artifact-free image with increased material differentiation. The CT system is also configured to acquire CT data, create a projection of material characteristics of the subject, and apply a weighting algorithm and/or color mapping to reconstruct a contrast-enhanced image that is substantially free of beam-hardening artifacts.

Therefore, in accordance with one aspect of the present invention, an imaging system is disclosed that includes a radiation source configured to project radiation toward an object to be scanned and an energy discriminating detector assembly having a plurality of detector elements and configured to detect radiation emitted by the radiation source and attenuated by the object to be scanned. The imaging system also includes computer programmed to count a number of photons detected by each detector element and associate an energy value to each counted photon and determine a material composition of a CT view from the number of photons counted and the energy value associated with each counted photon. The computer is also programmed to apply a weighting to the CT view based on the material composition of the CT view and reconstruct an image with differential weighting based on the weighting of the CT view.

In accordance with another aspect, the present invention includes a method of radiographic imaging is disclosed that includes the steps of acquiring energy discriminating CT data from an ROI and determining a material composition breakdown of the ROI from the energy discriminating CT data. The method also includes the steps of applying one or more weightings to the energy discriminating data based on the material composition of the ROI and displaying an image of the ROI from the energy discriminating CT data wherein portions of the image are weighted differently based on material composition.

According to another aspect of the present invention, a computer readable storage medium is disclosed having a computer program stored thereon and representing a set of instructions that when executed by a computer causes the computer to identify material characteristics of an ROI from energy discriminating CT data acquired from the ROI. The computer is also caused to weight the energy discriminating CT data associated with particular regions of the ROI based on the material characteristics identified in those regions and reconstruct an image of the ROI from the weighted energy discriminating CT data.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The present invention provides a system and method of reconstructing contrast-enhanced CT images that are substantially free of beam-hardening artifacts. The present invention is applicable with a photon counting (PC) radiographic system having a radiation energy detector configured to detect radiation energy at a given flux rate and output signals indicative of the detected radiation energy. The present invention is also applicable with an integrating energy selective detector, where the received radiation is registered in two or more energy ranges that may overlap through the use of either direct or indirect conversion detector materials using a layered design or depth of interaction to differentiate the energy bins. The present invention is also applicable with an energy integration detector and an x-ray source modulated to adjust the spectra for two or more different energy functions.

Figure 1:
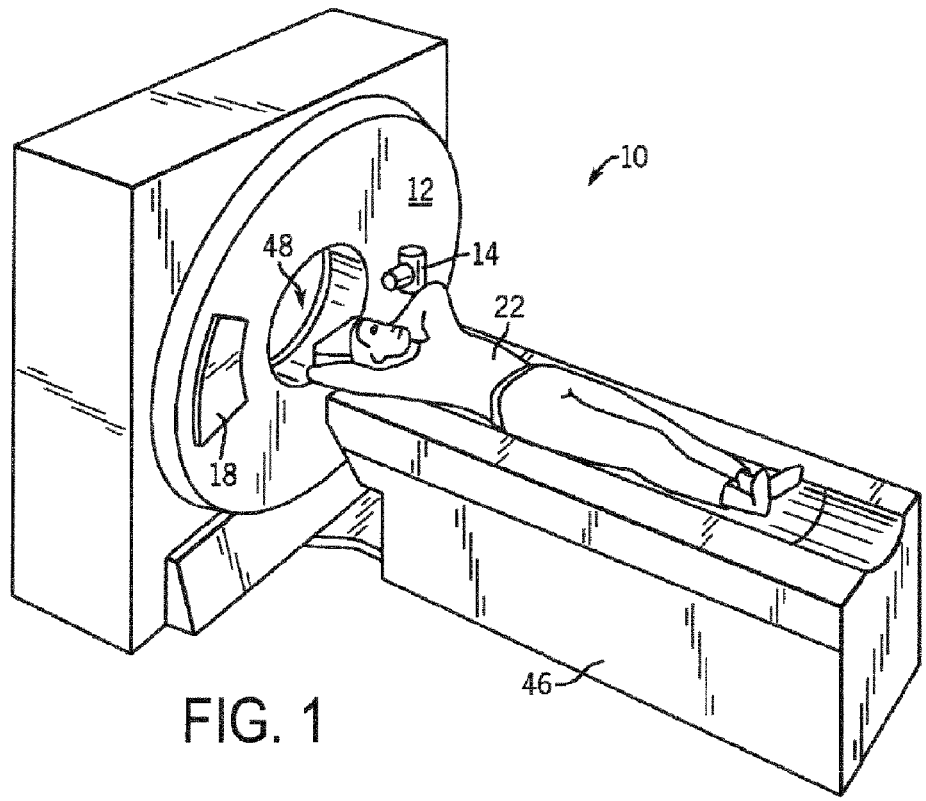
FIG. 1 is a pictorial view of a CT imaging system.
Figure 2:
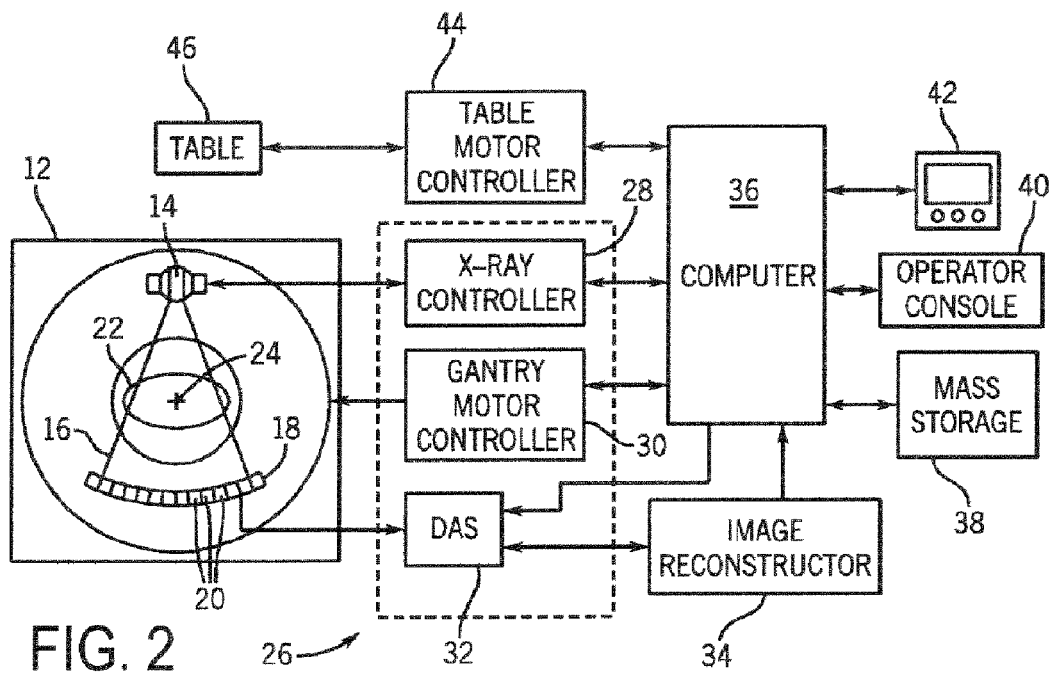
FIG. 2 is a block schematic diagram of the system illustrated in FIG. 1.

Referring now to FIGS. 1 and 2, a computed tomography (CT) imaging system 10 is shown as including a gantry 12 representative of a "third generation" CT scanner. The gantry 12 has an x-ray source 14 that projects a beam of x-rays 16 toward a detector assembly 18 on the opposite side of the gantry 12. The beam of x-rays is collimated by a collimator 19. The detector assembly 18 is formed by a plurality of detectors 20 which together senses the projected x-rays that pass through a medical patient 22. Each detector 20 produces an electrical signal that represents the intensity of an impinging x-ray beam and may also be capable of providing photon or x-ray count data and energy level, and hence the attenuated beam as it passes through the patient 22. During a scan to acquire x-ray projection data, the gantry 12 and the components mounted thereon rotate about a center of rotation 24.

Figure 3:
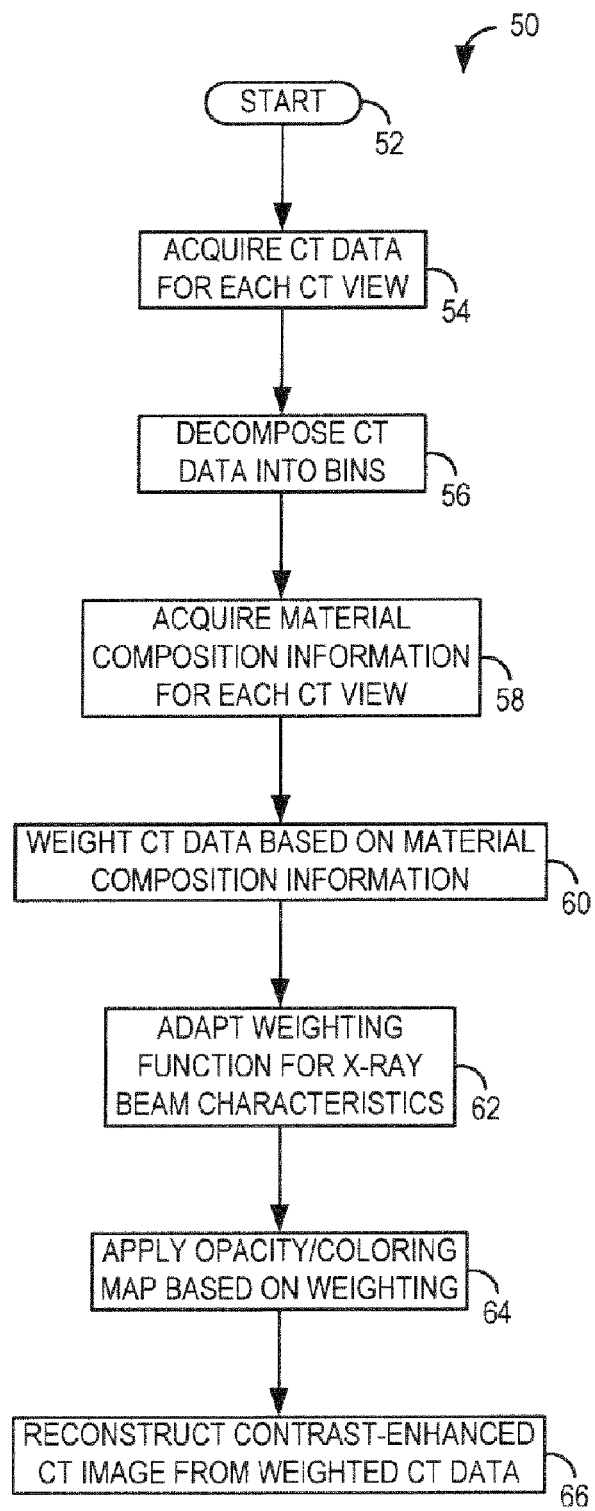
FIG. 3 is a flowchart illustrating the steps of a technique for reconstructing a contrast-enhanced image.

Rotation of the gantry 12 and the operation of the x-ray source 14 are governed by a control mechanism 26 of the CT system 10. The control mechanism 26 includes an x-ray controller 28 that provides power and timing signals to the x-ray source 14, a gantry motor controller 30 that controls the rotational speed and position of the gantry 12, and a collimator controller 29 that controls the collimator 19 to collimate the x-ray beam in the x (as shown in FIG. 2) and z directions (as shown in FIG. 3). A data acquisition system (DAS) 32 in the control mechanism 26 reviews data from the detectors 20 and converts the data to digital signals for subsequent processing. An image reconstructor 34 receives sampled and digitized x-ray data from the DAS 32 and performs high speed reconstruction. The reconstructed image is applied as an input to a computer 36 which stores the image in a mass storage device 38.

The computer 36 also receives commands and scanning parameters from an operator via console 40. An associated display screen 42 allows the operator to observe the reconstructed image and other data from the computer 36. The operator supplied commands and parameters are used by the computer 36 to provide control signals and information to the DAS 32, x-ray controller 28 and gantry motor controller 30. In addition, the computer 36 operates a table motor controller 44 which controls a motorized table 46 to position the patient 22 and gantry 12. Particularly, the table 46 moves portions of the patient 22 through a gantry opening 48.

In one embodiment, the CT system 10 is multi-energy computed tomography (MECT) system and is configured to be responsive to different incident x-ray spectra. This can be accomplished by acquiring projection data sequentially using different x-ray tube voltages. For example, two scans are acquired either back-to-back or interleaved in which the tube operates at 80 kVp and 160 kVp potentials, for example, generating a low and high energy spectrum, respectively. Alternatively, special filters may be placed between the x-ray source 14 and the patient 22 such that detector rows collect projections of different x-ray energy spectrum either sequentially or interleaved. Yet another embodiment is to use energy sensitive photon counting detectors such that each x-ray photon reaching the detector is recorded with its photon energy.

In yet another embodiment, energy sensitive detectors are used such that direct or indirect conversion material is used to separate photons into two or more energy bins that may overlap through the use of detector layers or depth of interaction detectors.

Multi-energy CT can reduce or substantially eliminate problems, such as lack of energy discrimination or material characterization, associated with some CT systems. In the absence of object scatter, the system 10 may be used to separately detect two regions of the incident photon energy spectrum, the low energy and the high energy portions of the incident x-ray spectrum. The behavior at any other energy can be derived based on the signal from the two energy regions. This technique is driven by the fundamental fact that in the energy region where CT is interested, two physical processes dominate the x-ray attenuation: (1) Compton scatter and (2) the Photoelectric effect. In order to characterize the behavior of an object causing attenuation of the x-ray beam, two independent parameters are measured. Thus, as will be described in detail, detected signals from the two energy regions provide sufficient information to resolve the energy dependence of the object being imaged; hence, the composition of the material can be characterized.

The data analysis used in MECT includes Compton and photoelectric decomposition and/or Basis material decomposition (BMD). In Compton and photoelectric decomposition, a pair of images is generated, which separately presents the attenuation from the Compton and photoelectric processes—instead of obtaining one image characterizing the overall attenuation coefficient in the reconstructed CT image. Also, a slight modification in the processing allows the generation of images representing density and effective atomic number. The BMD method is based on the concept that the x-ray attenuation of any given material in the energy range can be represented by a linear combination of a density mixture of other two known materials. These two materials are called the basis materials. Using BMD, two reconstructed images are obtained, each image representing the equivalent density of one of the basis materials. Since density is independent of x-ray photon energy, these images are relatively free of beam hardening artifacts. Additionally, the basis material is chosen to target a material of interest, thus enhancing the image contrast.

It should be noted that in order to optimize an MECT system not implementing energy discrimination with photon counting, large energy separation in the x-ray spectra should be achieved to increase image quality. Also, the photon statistics in these two energy regions should be comparable or the energy region with reduced statistical information may dominate the noise in the reconstructed image.

There are different methods to obtain dual energy measurements: (1) scan with two distinctive energy spectra, (2) detect photon energy according to penetration depth at the detector, or (3) photon counting with energy discrimination. Photon counting provides clean spectra separation and an adjustable energy separation threshold for balancing photon statistics.

While applicable with each of the aforementioned methods, the present invention will be further described with respect to an MECT system having energy discriminating radiation detectors capable of counting photon events and associating an energy level to a counted event.

Referring now to FIG. 3, the steps of a technique for contrast-enhanced imaging are set forth 50. Imaging contrast is enhanced based on weighting of photons received at a detector and the attenuation difference between a target material and background materials in the subject to be imaged. That is, in order to improve CNR in a given image, the technique 50 applies a tissue specific weighting function proportional to the attenuation difference between the target material and background material and adapts the weighting function according to x-ray beam characteristics.

The technique 50 starts at step 52 upon the acquisition of CT data for each CT view 54. The CT data acquired for each CT view 54 is decomposed by associating each of the acquired photons with a number of energy bins 56. Material composition information for each CT view is then acquired 58 based on the relative photon occupancy of bins into which the data was decomposed. In order to increase the image CNR, the technique 50 includes applying a tissue specific weighting function proportional to the attenuation difference between the target material and background material 60. Again, in the medical imaging x-ray energy range, there are two physical processes that dominate x-ray attenuation: photoelectric effects and Compton scatter. By ignoring k-edge effects, the interaction cross-section for these two processes decreases as the x-ray energy increases. The x-ray attenuation coefficient difference between two materials also decreases as the x-ray energy increases. Therefore, low energy x-rays carry more information or generates more material distinguishing contrast than high energy x-rays. Therefore, low energy x-rays can be weighted heavier than high energy x-rays in order to maximize the contrast of material differences. The attenuation coefficient difference between high atomic number material and the water is large at low energy, the low energy x-rays are weighted heavily to boost the CNR for these high z materials. For low z materials that have similar attenuation energy dependence as water, the weighting function would be more uniform.

For example, since the attenuation coefficient difference between a high atomic number material and water is large at low energy, low energy x-rays are weighted heavily to boost the CNR for high z materials. Furthermore, the technique 50 applies a uniform weighting to low z materials that have similar attenuation energy dependence. By utilizing a uniform weight function for low z materials, low image noise of PC system is preserved. Accordingly, in applications that visualize multiple materials, multiple images can be obtained by using the tissue specific weighing function for each material. Additionally, the increased CNR for high z materials can reduce subject dose requirement for some applications.

In order to minimize the performance degradation due to detector noise or a limited number of the detector energy bins used to decompose the CT data 56, the weighting function can also be adapted 62 according to the x-ray attenuation and energy characteristics of the particular materials of interest. That is, the technique can adaptively take the image noise into account in order to select the optimum weighting function 60, 62 to enhance each target material. Furthermore, each material or mixture of materials can be associated with a point in a 2D material decomposition (2DMD) plot. Accordingly, an anatomical region in the CT view is coordinated with corresponding points in the 2DMD plot to yield information about the composition of the anatomical region of the subject to be imaged and apply contrast enhancements to highlight composition variations.

That is, once the CT data is properly weighted 60, 62, opacity/color mapping is applied according to the applied weighing function 64 to reconstruct a contrast-enhanced CT image 66. As will be illustrated with respect to FIGS. 11-14, images with different weighting functions can be examined individually or combined together to form composite image with different regions of the image using different weighting functions. Furthermore, if the images are combined, intensity/color maps may be applied to form an image with material variations reflected in color, hue, and/or intensity variations. For example, the technique 50 may combine density and atomic number information available from energy discrimination CT imaging and apply the information as inputs to specific visualization algorithms such as color or grey-scale mapping and segmentation 64 to reconstruct an image with enhanced contrast 66.

By applying the tissue-specific 60 and beam-characteristic weighting function 62, the contrast information carried by different x-ray energies are effectively used for a particular application and produce an image with enhanced contrast 66. The reconstructed image 66 has improved conspicuity of particular tissues in the body and substances. For example, instruments or contrast agents that may be introduced into the body appear more conspicuously within the reconstructed image 66. Similarly, other tissues or substances may be displayed in the same image with reduced contrast or removed from the image in order to tailor the image to a particular examination target.

Therefore, it is contemplated that multiple weighting functions can be selected to enhance the visibility of different materials in separate images. The target materials and weighting functions can be pre-selected before the analysis for certain studies where known material differences are expected because of the common anatomy of subjects. Similarly, the level of detector noise or energy resolution may be assumed to select the optimum weighting function. Furthermore, the target materials and weighting functions can be identified adaptively with the image segmentation algorithms that search both the image domain and materials decomposition space.

Figure 4:
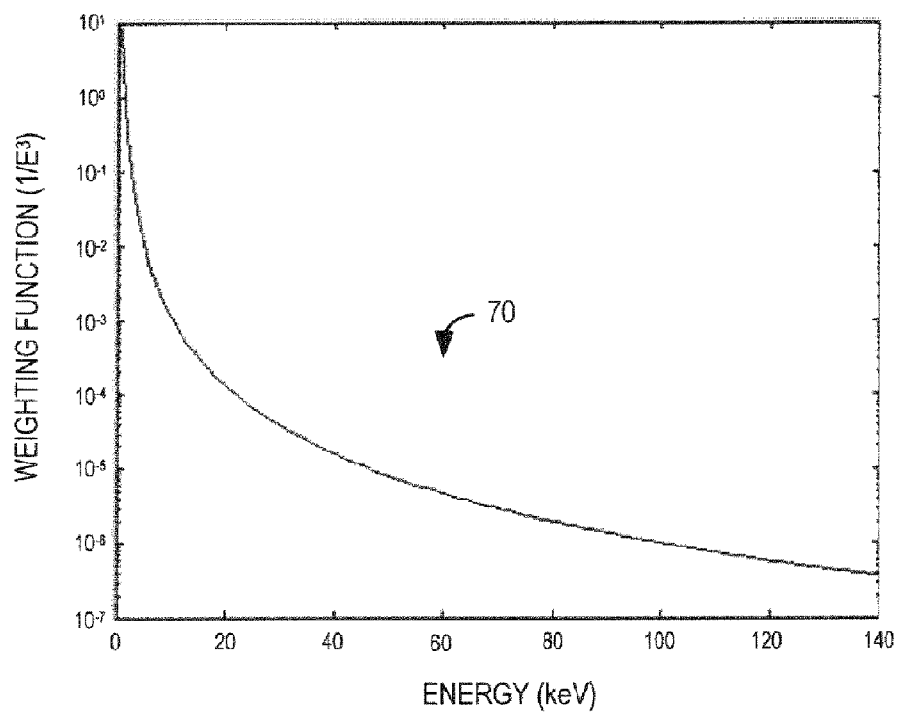
FIG. 4 is a graph showing one exemplary weighting algorithm applicable with the weighting technique in FIG. 3.
Figure 5:
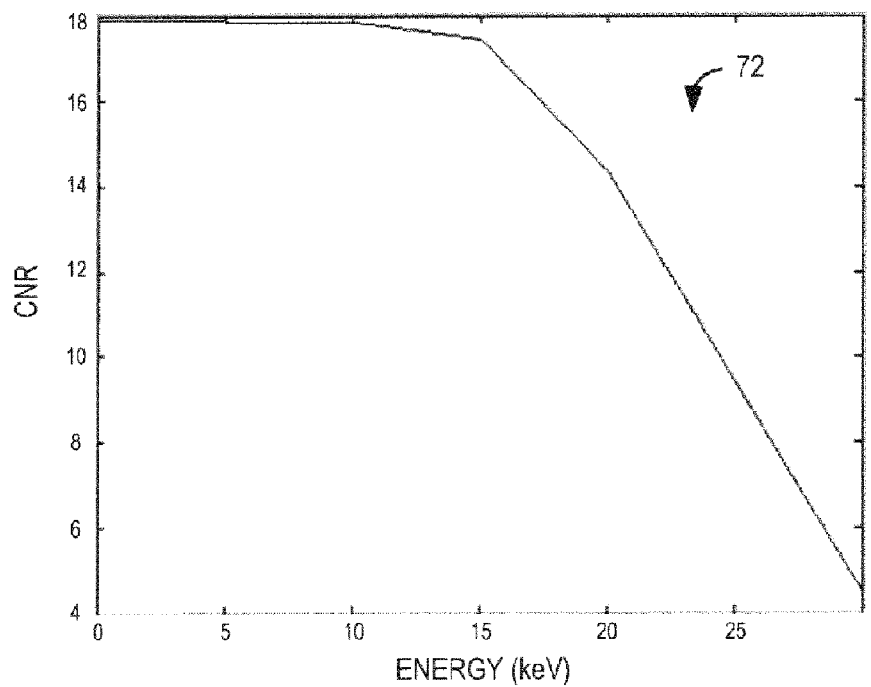
FIG. 5 is a graph showing increased CNR upon applying the weighting algorithm of FIG. 4.

Referring now to FIGS. 4 and 5, graphs illustrating an exemplary weighting function over various energy levels 70 and corresponding image CNR across detector energy resolution 72 are shown. FIG. 4 shows a 1/E weighting function 70. As shown in FIG. 5, when the weighting function 70 is applied to acquire CT data, the finite detector energy resolution significantly impacts the CNR for optimal energy weighting (OEW) 72. Therefore, the data available from an energy sensitive detector allows the production of an improved attenuation value by performing OEW.

Figure 6:
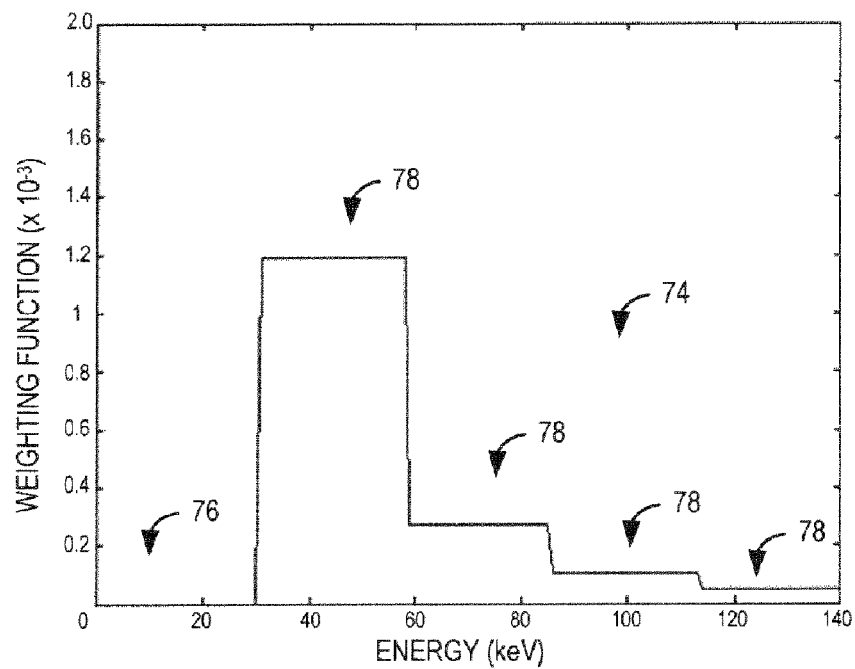
FIG. 6 is a graph showing another exemplary weighting algorithm applicable with the weighting technique in FIG. 3.
Figure 7:
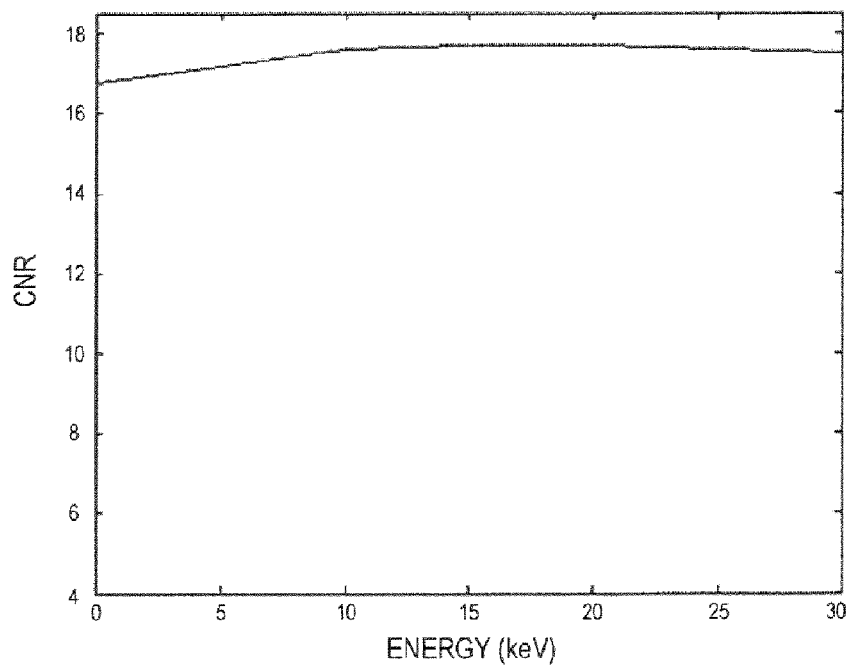
FIG. 7 is a graph showing increased CNR upon applying the weighting algorithm of FIG. 6.

Referring to FIGS. 6 and 7, the impact of detector energy resolution on the CNR for OEW can be reduced by applying a threshold to modify the weighting function and/or applying a discrete or stepped weighting function 74. Specifically, FIG. 6 shows that the weighing function 74 may include a threshold that reduces the effect of the weighting function 74 at lower energy levels 76. Furthermore, FIG. 6 shows that the weighting function 74 may include multiple discrete steps 78 as opposed to an analog slope, as shown in FIG. 4. In this case, the impact of detector energy resolution on the CNR for OEW can be reduced, as shown in FIG. 7. Accordingly, upon applying a proper weighting function, the finite detector energy resolution has a reduced effect on the CNR for OEW.

Figure 8:
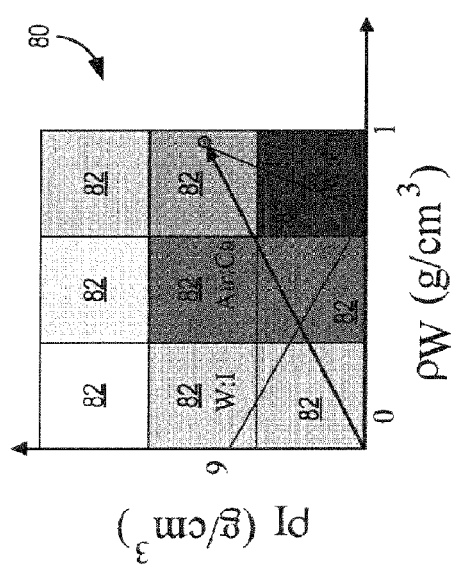
FIG. 8 is an illustration of one embodiment for segmenting an image based on material decomposition.
Figure 10:
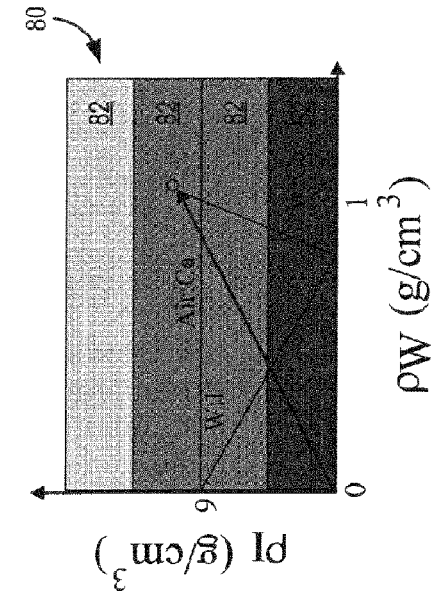
FIG. 10 is an illustration of yet another embodiment for segmenting an image based on material decomposition.
Figure 9:
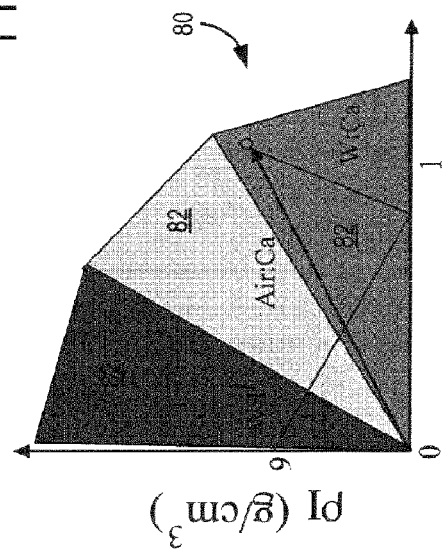
FIG. 9 is an illustration of another embodiment for segmenting an image based on material decomposition.

As described with respect to FIG. 3, by decomposing the acquired CT data into bins, material composition information can be acquired for each CT view. Material decomposition provides two additional numbers to characterize each material characteristic or each voxel in a CT data set. These two numbers are the densities of two basis materials. Referring now to FIGS. 8-10, the pair of basis densities can be represented as a point within a plane 80 defined by a basis data set. In addition to these two basis density numbers, an attenuation value of a given voxel is also available through analysis of the acquired CT data. Thus, in total, three numbers are available to characterize a given voxel and provide a basis for opacity/color mapping.

To differentiate materials which may have similar x-ray attenuation values, the two dimensional plane 80 is divided into sections 82 such that data falling into a particular section 82 of the plane 80 is tagged by labels which can, for example, represent the mean atomic number of the object. These labels are utilized as inputs for segmentation and application of color mapping to an image. FIGS. 8-10 illustrate some exemplary segmentation schemes; however, virtually any segmentation scheme may be utilized or preferred for a particular imaging application.

Segmentation is defined here as the deemphasizing/removal of certain object(s) in the reconstructed image. The pixels associated with the CT data that is to be segmented is set to a neutral or background gray-scale value. Therefore, in this display mode, certain anatomical structures that are not of particular clinical interest and which could interfere with the visualization of a desired anatomical feature or cause "clutter" are deemphasized/removed.

Furthermore, the selection/adaptation of the energy weighting function can improve the performance of the system with respect to differentiating materials in the reconstructed image. Specifically, the 2DMD plots 80 may be utilized to achieve adaptively identified weighting functions. Thus, the coordination of an anatomical region in the CT image with the corresponding points in the 2DMD plot gives information about the composition of those anatomical regions of the object under study. By applying an adaptive algorithm, this information can be used to recalculate the CT energy-weighted image with a specific weighting function determined by a first pass iteration.

Therefore, the two basis density values and the attenuation value obtained from the data processing using an energy sensitive detector can be used in a variety of ways to display an image so as to improve the diagnostic value of the image data. For example, the information can be utilized for labeling voxels for segmentation. In this case, the data from voxels having certain labels will be removed from the image by setting the magnitude of the voxel data to match that of background data and allowing the data of the remaining voxels to retain their attenuation values. The segmentation algorithm may also combine other conventional segmentation techniques to better search and extract the relevant anatomy such as the above-described color and/or intensity mapping.

That is, it is contemplated that the two basis density values and the attenuation value may be utilized to apply an attenuation intensity map with discrete color mapping. In this case, instead of removing the object from the reconstructed image, as described for segmentation, the label can be used to code the hue value of the image pixel. Additionally, it is contemplated that color mapping may be performed using only the basis density values. In this case, the ratio of basis density values may be used to code the hue and the intensity value is encoded based on the quadrature sum of the two basis density values.

Similarly, the values can be used to apply an attenuation intensity map with continuous color mapping. In accordance with one embodiment, the image is displayed with the intensity of each pixel coded to correspond to the attenuation value but the hue is coded continuously based on the ratio of the two basis density values, which is indicative of the angle in the basis plane.

Additionally, three-dimensional (3D) visualization techniques may be performed based on the two basis density values and the attenuation value. It is contemplated that any number of opacity functions weighted by the basis density values can be used to display the 3D data set. For example, a maximum intensity projection through a 3D data set of one basis density value may be used to generate a visualization of a given object and its similarity to the basis material. Furthermore, the data available from an energy sensitive detector allows the production of an improved attenuation value by performing OEW.

Referring now to FIGS. 11-14, the atomic number information may be used to clearly differentiate materials in the body and/or enhance the visibility of one material relative to another. Accordingly, visualization of iodine and other contrast agents, which either flow in vascular vessels attached through functional agents to target tissue or perfuse into body tissues over a metered period of time, is improved.

Figure 11:
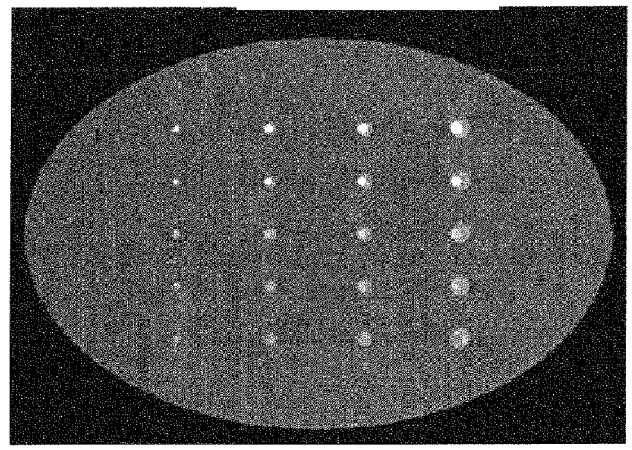
FIG. 11 is an illustration of a conventional CT image.
Figure 12:
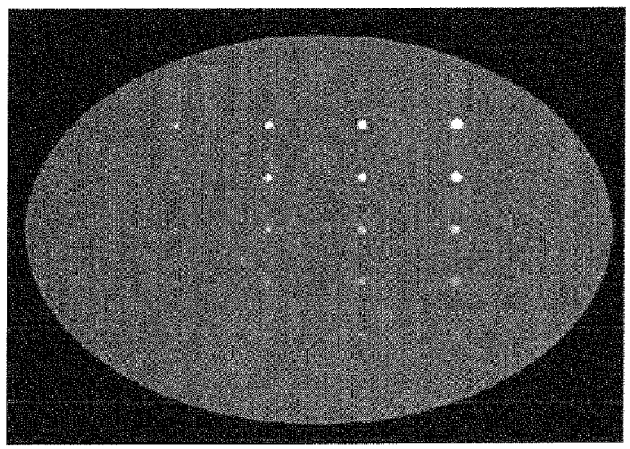
FIG. 12 is an illustration of an EDCT image reconstructed from decomposed data attributable to water according to the technique of FIG. 3.
Figure 13:
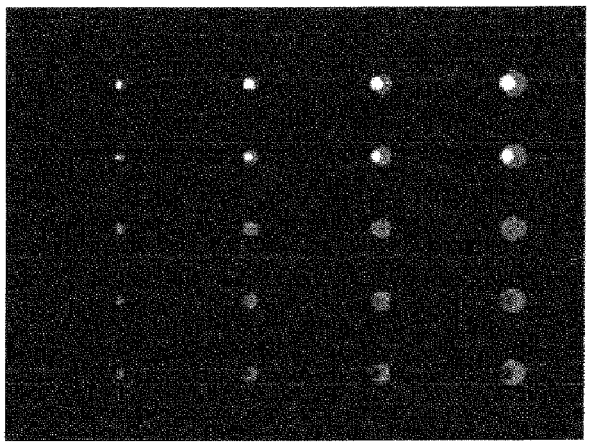
FIG. 13 is an illustration of an EDCT image reconstructed from decomposed data attributable to iodine according to the technique of FIG. 3.
Figure 14:
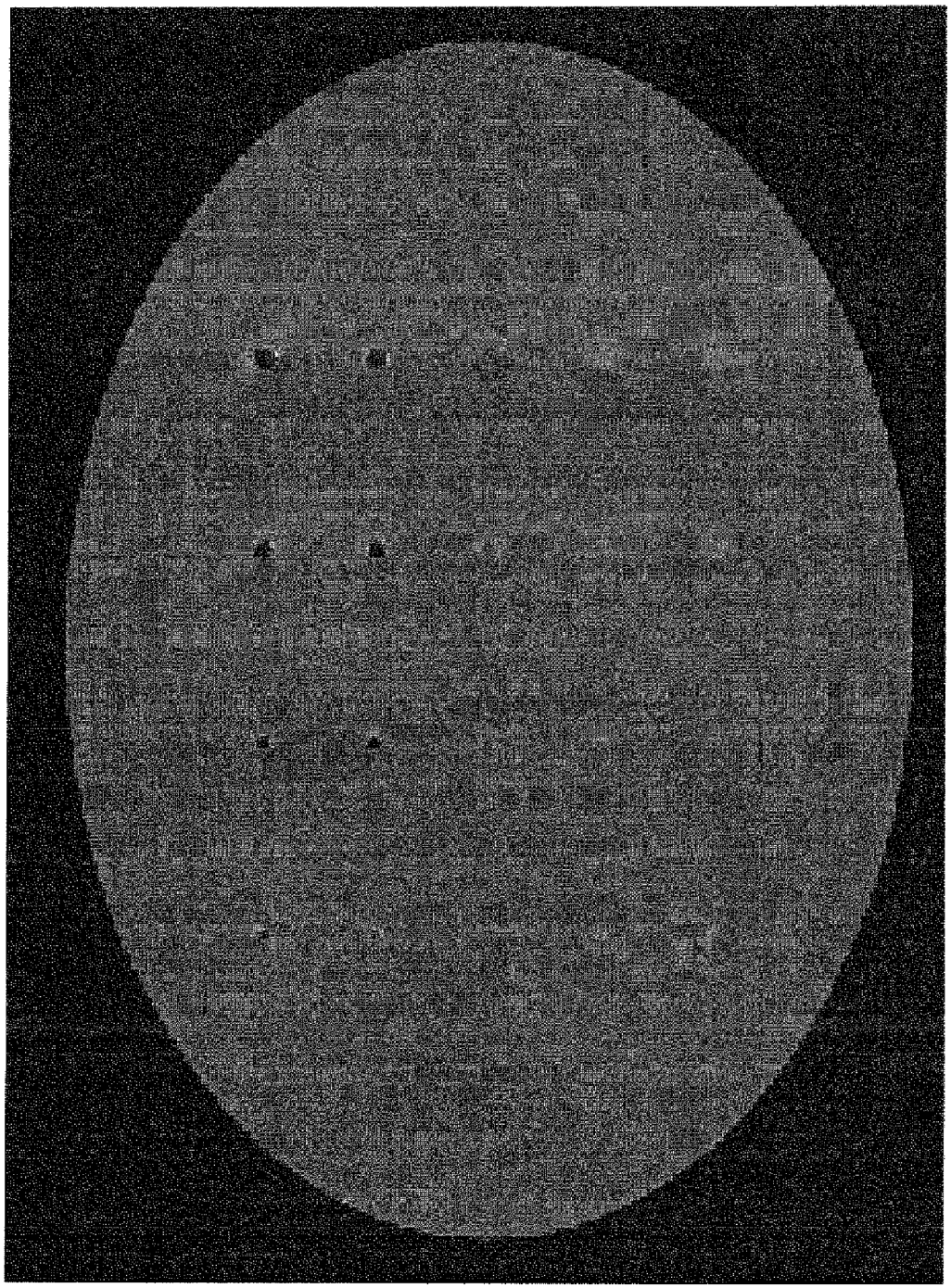
FIG. 14 is an illustration of an EDCT image combining the conventional CT data and decomposed CT data that is segmented to show material decomposed according to the technique of FIG. 3.

For example, FIG. 11 shows a conventional CT image that, as previously described, can be individually reconstructed and examined. Similarly, FIG. 12 shows an individually reconstructed water image. Additionally, FIG. 13 shows an individually reconstructed iodine image. In each case, the materials are clearly differentiated and unimpeded or "cluttered" by other materials. Furthermore, FIG. 14 shows a combination of the individual images shown in FIGS. 11-13. In this case, the information shown in the individual conventional, water, and iodine images are reflected as variations in hue, saturation, and value. For example, information attributable to water is represented by variations in hue, information attributable to iodine is shown by saturation changes, and information attributable to the conventional image is reflected by value adjustments.

As previously stated, the material decomposition algorithm can be applied to create a CT image not subject to beam hardening artifact. The material decomposition algorithm can separate data attributable to distinct materials of the subject into a set of basis material's density. By accurately approximating the contents of the basis material within the subject to be imaged, the projection can be remapped according to the attenuation characteristics of the basis materials and an attenuation calculation performed to yield a reconstructed image substantially free of beam hardening artifacts.

Figure 15:
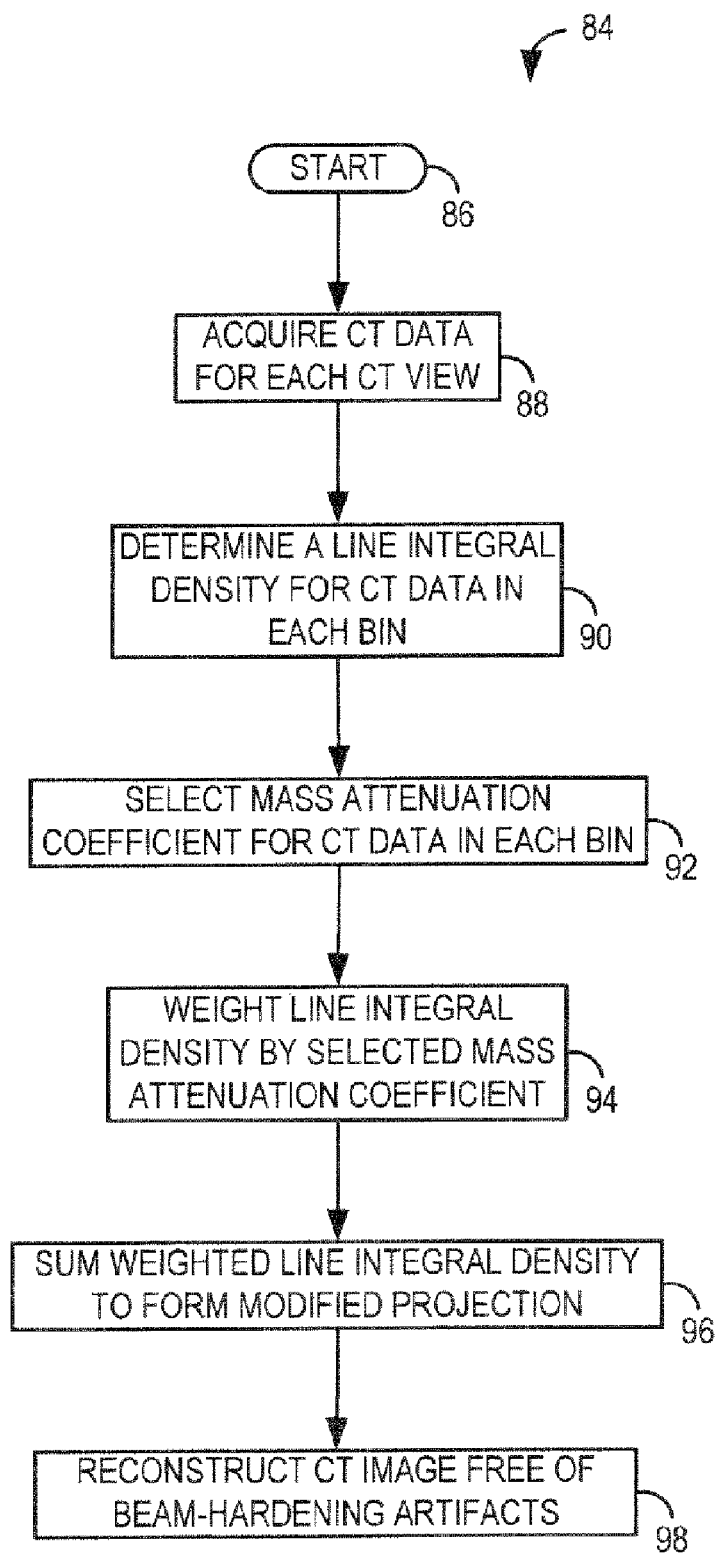
FIG. 15 is a flowchart illustrating the steps of a technique for reducing beam-hardening artifacts within CT images.

Referring now to FIG. 15, the steps of a technique 84 for reconstructing an image substantially free of beam-hardening artifacts are set forth. The technique 84 starts at step 86 with the acquisition of CT data for each desired CT view 88. The acquired CT data 88 is then decomposed based on at least two basis materials into bins corresponding to a respective basis material.

To perform the decomposition, a decomposition algorithm is applied to the energy sensitive projection data. A line integral density is determined for the CT data in each bin 90. The average mass attenuation coefficients for each material are calculated by using spectrum weighting values derived as a function of energy obtained from established databases 92. The line integral density is then weighted by the selected mass attenuation coefficients 94. The weighted line integral density is then summed to calculate a new projection 96. That is, to obtain the attenuation value of some material property at every point in the reconstructed image creates a "projection" of this property, which is a line integral of this property. In this case, since the new projection 96 is linear with material path lengths, an image reconstructed from the new projection set will be substantially free of beam hardening artifacts 98. For example, a given material or mixture of materials will have a constant CT number appropriate to that material regardless where it is in the field of view.

In addition to using average mass attenuation coefficients in the construction of a new projection, it is possible to construct the new projection using the attenuation for any particular energy. More generally, it is possible to arbitrarily select a fixed set of basis material coefficients to emphasize the desire basis material characteristics in the reconstructed image 98. For example, should water and bone be selected as basis materials, it is possible to arbitrarily select a fixed set of bone and water coefficients to emphasize the bone-like or water-like character of the object in the reconstructed image. In this case, as long as the new projection has the same contribution from a material independent of the position in the object, the reconstructed image will be substantially free of beam-hardening artifacts.

Figure 16:
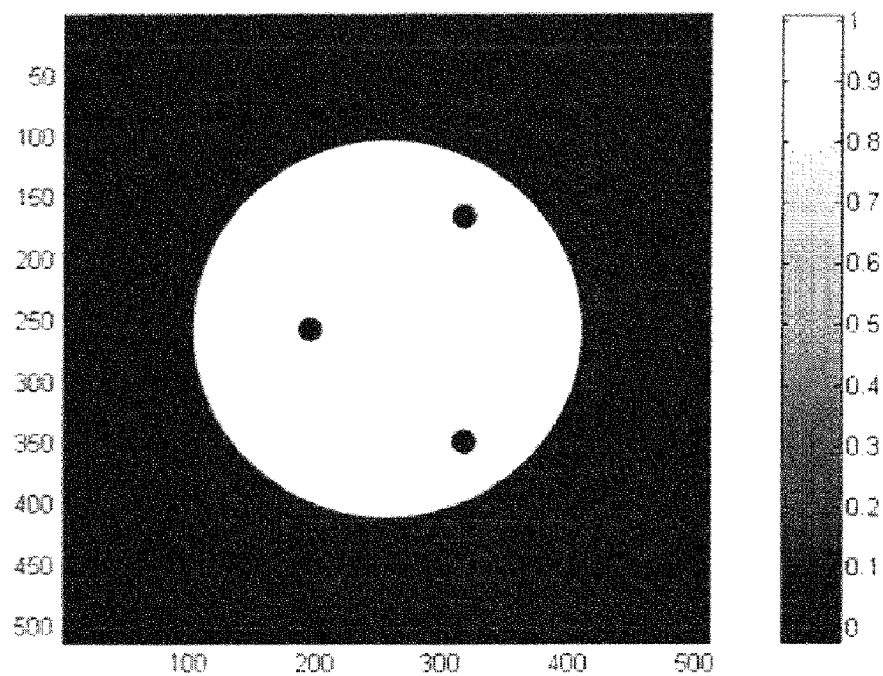
FIG. 16 is an illustration of an EDCT image reconstructed according to the technique in FIG. 15 from decomposed data attributable to water.
Figure 17:
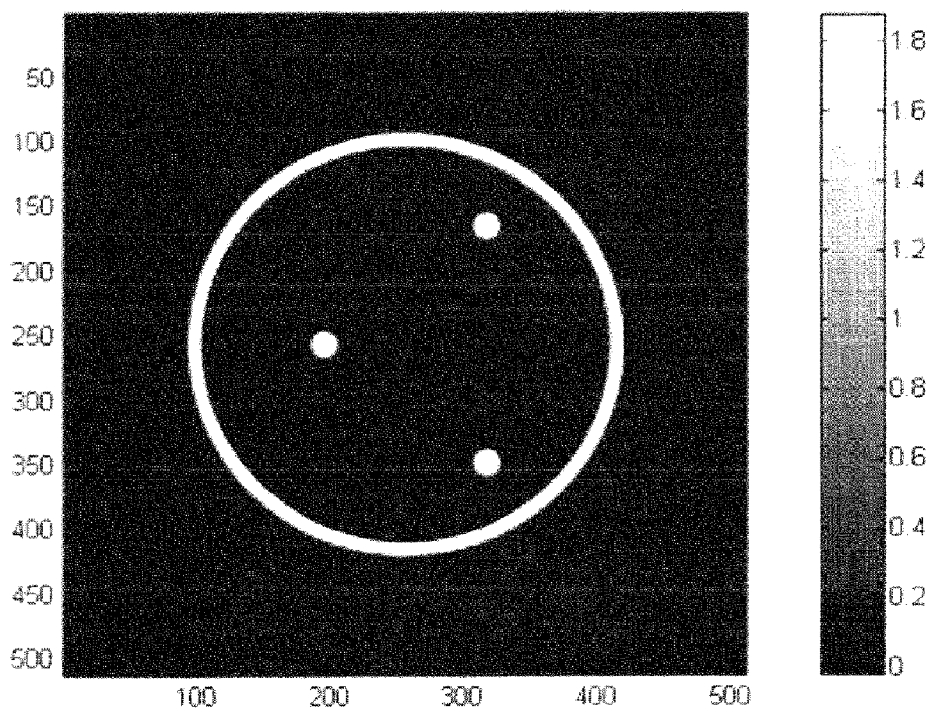
FIG. 17 is an illustration of an EDCT image reconstructed according to the technique in FIG. 15 from decomposed data attributable to bone.
Figure 18:
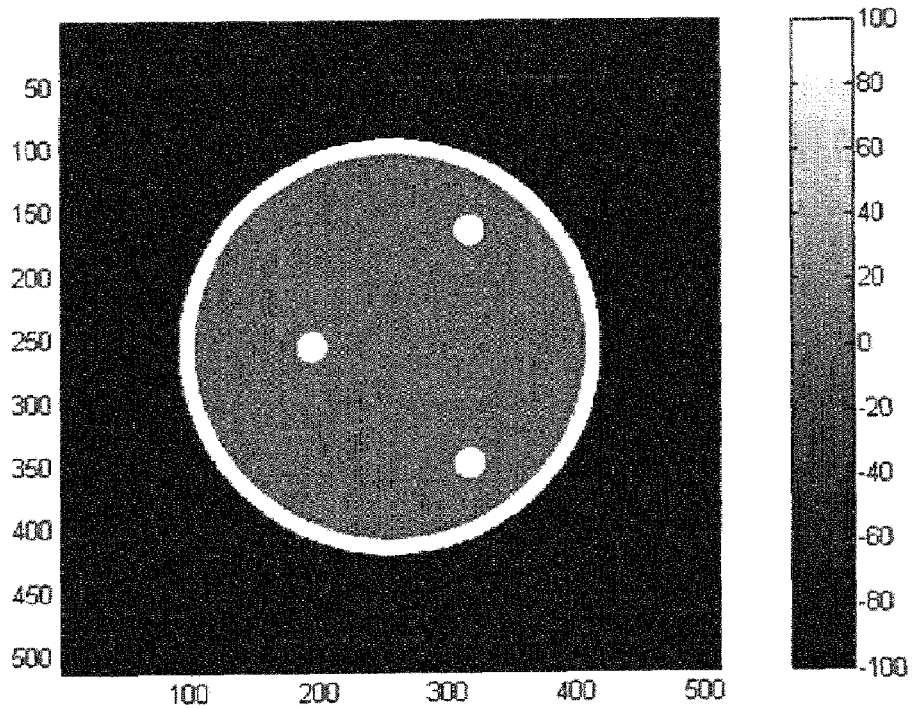
FIG. 18 is an illustration of an EDCT image reconstructed according to the technique in FIG. 15 that is substantially free of beam-hardening artifacts.
Figure 19:
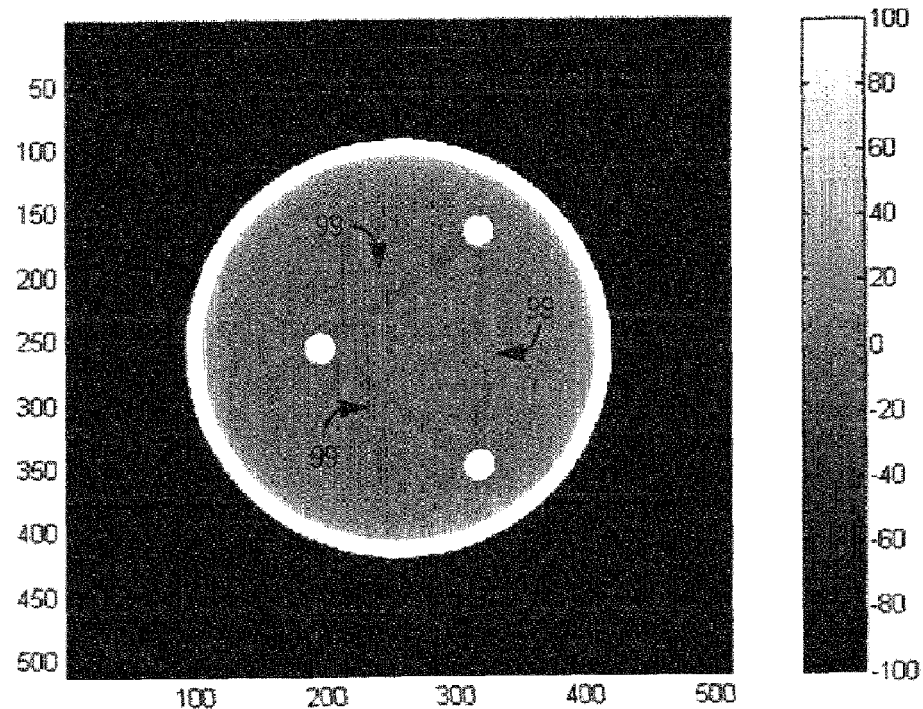
FIG. 19 is an illustration of a known CT image with beam-hardening artifacts.
Figure 20:
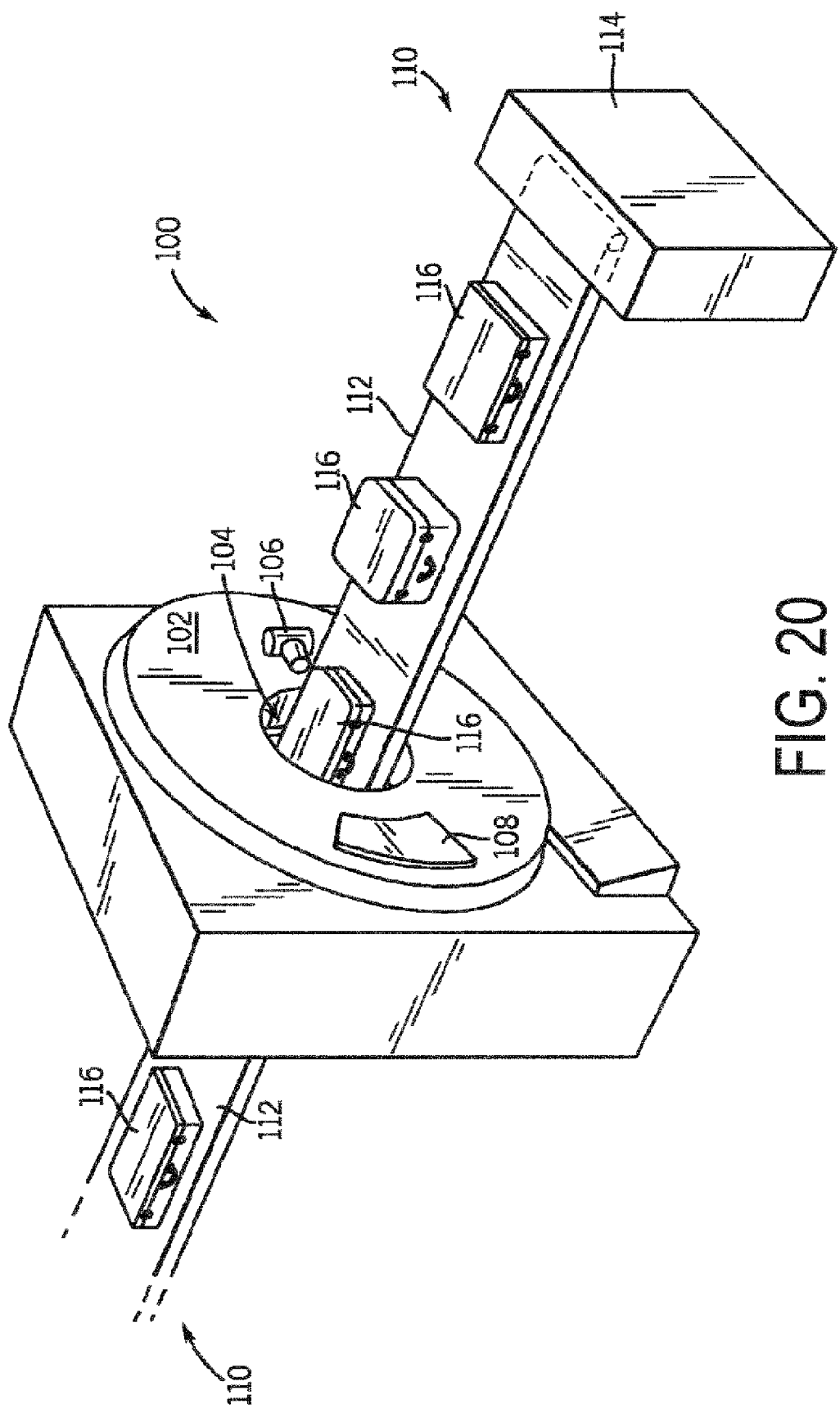
FIG. 20 is a pictorial view of a CT system for use with a non-invasive package inspection system.

FIGS. 16 and 17 show exemplary images reconstructed from CT data subjected to the above-described material decomposition technique 84 of FIG. 15. In particular, FIG. 16 shows a water image substantially free of beam-hardening artifacts and FIG. 17 shows a bone image substantially free of beam-hardening artifacts. These individual images can be combined into a reconstructed image that is free of beam-hardening artifacts, as shown in FIG. 18. The absence of beam-hardening artifacts is particularly evident when compared with a conventionally reconstructed image, as shown in FIG. 19. In FIG. 19, bone-induced beam-hardening artifacts 99 are clearly visible as darkened shading connecting the bone regions of the image.

It is recognized that bone and water have been referred to as exemplary basis materials. However, any two different basis materials may be utilized. For example, fat and aluminum are equally suitable basis materials and, upon application of the above-described material decomposition technique, will yield a reconstructed image that is substantially free of beam-hardening artifacts.

Therefore, by applying the above-described technique or attenuation calculation algorithm with energy discrimination projection data, beam-hardening artifacts are substantially eliminated within the reconstructed image. Moreover, the CT number in the reconstructed image will only depend on the material composition for a particular pixel and enable numerous quantification applications of the CT images.

Referring now to FIG. 22, a package/baggage inspection system 72 may be equipped with a microprocessor or other computing device to carry out the techniques described herein. The inspection system 72 includes a rotatable gantry 74 having an opening 76 therein through which packages or pieces of baggage may pass. The rotatable gantry 74 houses a high frequency electromagnetic energy source 78 as well as a detector assembly 80. A conveyor system 82 is also provided and includes a conveyor belt 84 supported by structure 86 to automatically and continuously pass packages or baggage pieces 88 through opening 76 to be scanned. Objects 88 are fed through opening 76 by conveyor belt 84, imaging data is then acquired, and the conveyor belt 84 removes the packages 88 from opening 76 in a controlled and continuous manner. As a result, postal inspectors, baggage handlers, and other security personnel may non-invasively inspect the contents of packages 88 for explosives, knives, guns, contraband, etc.

Therefore, the above-described technique utilizes a tissue-specific weighting function to increase CNR for x-ray imaging. The weighting function may be adapted according to the x-ray beam characteristics to minimize the CNR degradation due to the detector noise and a limited number of the energy bins. The adaptive system uses the 2DMD plot to tag materials in the image and select the appropriate weighting function. An image visualization algorithm is used to combine the decomposed CT data to reconstruct a composite contrast-enhanced image.

Additionally, the technique combines the use of basis density values, multiple material decomposition labels, and attenuation values to encode values of pixels in an image. Similarly, segmentation and 3D visualization are utilized to combined CT data and generate opacity/color mapping functions for image reconstruction. Furthermore, the technique combines conventional CT visualization techniques and segmentation with energy sensitive derived parameters.

A number of techniques are provided to reconstruct contrast-enhanced images. Specifically, CT data labels can be used as a basis for segmentation. In this case, data for voxels having certain labels may be removed from the image by setting the magnitude of the data for the voxels to a background level. Alternatively, instead of removing the data for these "background" voxels from the image, the label can be used to code the hue value for the pixel corresponding to the voxel and apply an attenuation intensity map to perform discrete color mapping. Additionally, the attenuation intensity map may be applied with continuous color mapping to reconstruct an image with the intensity of the voxel coded by the attenuation value. In this case, the hue is coded in a continuous manner by the ratio of the two basis density values. Color mapping can also be applied based on the basis density values. Accordingly, the ratio of basis density values is used to code hues such that the intensity value is enclosed by the quadrature sum of the two basis density values. Also, 3D visualization can be performed by using any number of opacity functions weighted by the basis density values to reconstruct a 3D data set into a contrast-enhanced image. Furthermore, the availability of data from energy sensitive detectors allows the production of improved attenuation values by performing optimal energy weighting. Therefore, the images can enhance the visibility of specific features or tissues of an object under study. The techniques also substantially remove beam-hardening artifacts that could interfere with the desired image.

The aforementioned technique may be utilized with a variety of CT-type imaging systems. Specifically, it is contemplated that the present invention may be utilized with multi-energy systems having energy discriminating radiation detectors capable of counting photon events and associating an energy level to a counted event. Such detectors are susceptible to saturation. Therefore, to combat saturation of these detectors, a number of saturation techniques may be used.

Generally, high-sensitivity photon counting radiation detectors are constructed to have a relatively low dynamic range. This is generally considered acceptable for photon counting detector applications since high flux conditions typically do not occur. In CT detector designs, low flux detector readings through the subject are typically accompanied by areas of high irradiation in air, and/or within the contours of the scan subject requiring CT detectors to have very large dynamic range responses. Moreover, the exact measurement of photons in these high-flux regions is less critical than that for low-flux areas where each photon contributes an integral part to the total collected photon statistics. Notwithstanding that the higher flux areas may be of less clinical or diagnostic value, images reconstructed with over-ranging or saturated detector channel data can be prone to artifacts. As such, the handling of high-flux conditions is also significant.

An x-ray flux management control is designed to prevent saturation of PC x-ray systems having detector channels characterized by low dynamic range. Dynamic range of a detector channel defines the range of x-ray flux levels that the detector channel can accept and still provide meaningful data at the low-flux end and not experience over-ranging or saturating at the high flux end. Notwithstanding the need to prevent over-ranging and to provide diagnostically valuable data, the handling of low-flux conditions, which commonly occur during imaging through thicker cross-sections and other areas of limited x-ray transmission, is also critical in detector design.

Figure 21:
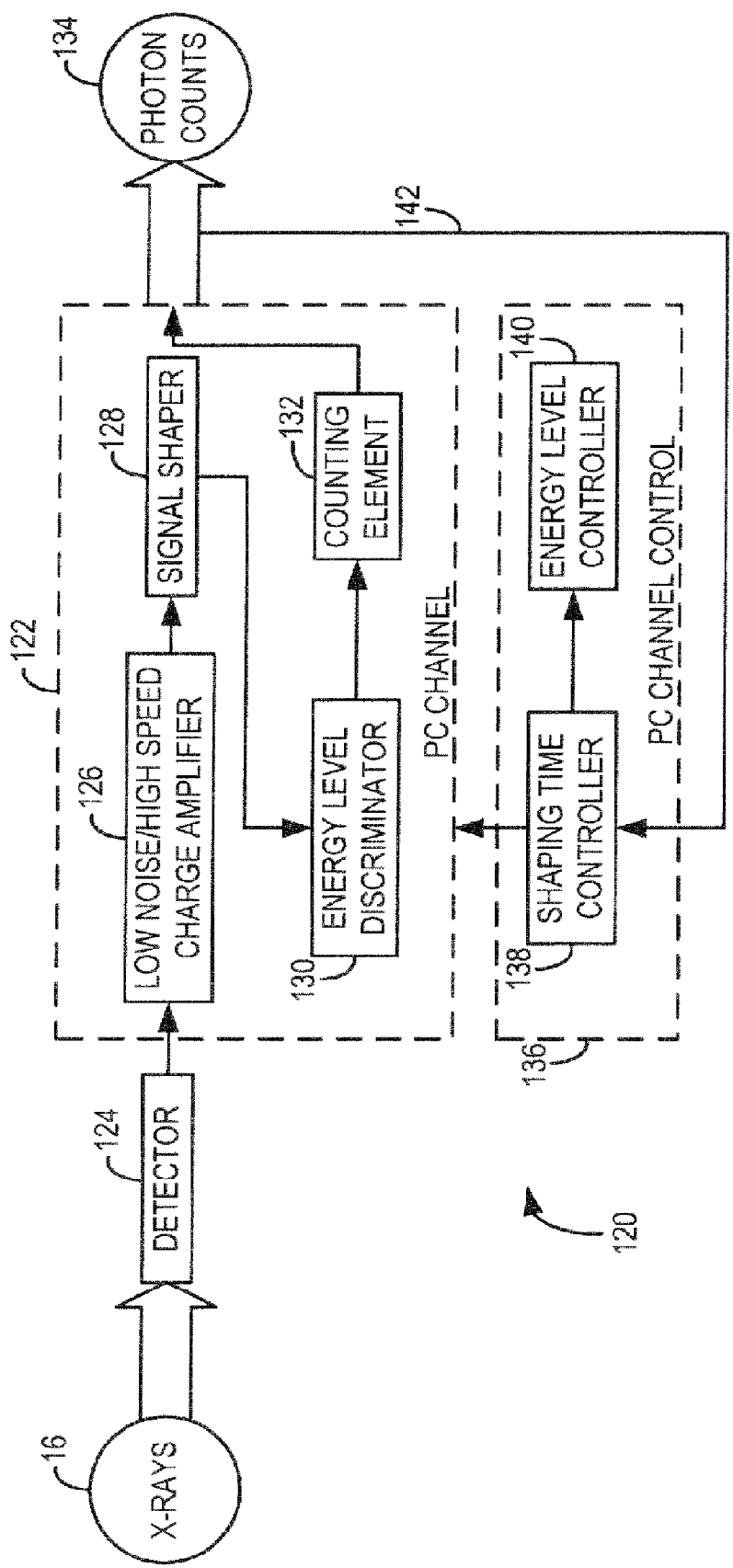
FIG. 21 is a block schematic diagram of a preferred x-ray detection system.

One such MECT system is set forth in FIG. 21. Specifically, FIG. 21 shows a block schematic diagram of an x-ray detection system 120 applicable with the present invention. The system 120 includes a PC channel 122 connected to receive electrical signals from a detector element 124. The detector 124 is constructed to detect x-rays 16 projected by an x-ray source and attenuated by a subject, such as a medical patient. It is understood that the present invention is applicable with gamma rays and other forms of radiographic energy.

The PC channel 122 includes a low-noise/high-speed charge amplifier 126 connected to receive the electrical signals from detector element 124. The amplified output of the amplifier 126 is then input to a signal shaper 128 constructed to extract individual photon events from the electrical signals. An energy level discriminator 130 is connected to the signal shaper 128 and is designed to filter photons based on their pulse height energy level relative to one or more thresholds. To this end, those photons having energy levels outside a desired range are excluded from counting and processing for image reconstruction. Minimally, the discriminator 130 is designed to exclude those photons having an energy level corresponding to noise in the system. It is contemplated that multiple thresholds may be used to define energy level ranges. A counting element 132 receives those photons not filtered out by the energy level discriminator 130 and is constructed to count the number of photons received at the detector and provide a corresponding output 134.

The PC channel 122 is operationally connected to a control 136 that includes a shaping time controller 138 and, preferably, an energy level controller 140. While it is preferred that control 136 include the energy level controller 140, it is contemplated that the present invention may be carried out without it. In one embodiment, the PC channel 122 includes an active filter whose operation defines the shaping time of the PC channel 122. In this regard, resistive and capacitive characteristics of the active filter can be adjusted to manipulate the channel's shaping time properties.

The shaping time controller 138 is connected to the PC channel 122 and is designed to adjust the shaping time characteristics of PC channel 122 based on photon count feedback received across feedback loop 142. More particularly, the shaping time controller 138 increases the shaping time of the PC channel 122 when the detector element 124 is exposed to low x-ray flux as measured by the number of photons counted 134. In contrast, when the x-ray flux on the detector element 124 increases, the time shaping controller decreases the time shaping or sampling window of the PC channel 122.

As such, when the detector is experiencing higher x-ray flux, the amount of time the PC channel 122 spends sampling the photon charge cloud is reduced. Accordingly, less precise photon and energy discriminatory data with respect to the photon charge cloud is determined; however, the PC channel 122 recovers at a rate sufficient to avoid over-ranging. In this regard, as the shaping time or sampling window is caused to decrease, more photons are inspected for data, i.e. counted, while each detected photon provides less precise energy discriminatory information. And, under high flux conditions, each individual photon assumes less importance and the overall system performance and image quality is minimally impacted by the reduced SNR. On the other hand, when the detector 124 is experiencing lower x-ray flux, the amount of time the PC channel 122 spends to sample the photon charge cloud is lengthened which allows sufficient time to sample the entire photon charge cloud and attain relatively precise photon count and energy discriminatory data.

As referenced above, the control 136 includes, in one embodiment, an energy level controller 140. Since the measured photon signal levels vary with channel shaping time, the automatic energy discriminator energy level controller 140 is coupled to shaping time controller 138 and the PC channel 122 to adjust or otherwise calibrate the energy level threshold of the PC channel 122 in response to an adjustment in the shaping time. By performing appropriate channel calibration, photons having an acceptable or decreased energy level are counted to assure linear energy response independent of channel shaping time and count rate.

Therefore, an imaging system is disclosed that includes a radiation source configured to project radiation toward an object to be scanned and an energy discriminating detector assembly having a plurality of detector elements and configured to detect radiation emitted by the radiation source and attenuated by the object to be scanned. The imaging system also includes computer programmed to count a number of photons detected by each detector element and associate an energy value to each counted photon and determine a material composition of a CT view from the number of photons counted and the energy value associated with each counted photon. The computer is also programmed to apply a weighting to the CT view based on the material composition of the CT view and reconstruct an image with differential weighting based on the weighting of the CT view.

The present invention also includes a method of radiographic imaging is disclosed that includes the steps of acquiring energy discriminating CT data from an ROI and determining a material composition breakdown of the ROI from the energy discriminating CT data. The method also includes the steps of applying one or more weightings to the energy discriminating data based on the material composition of the ROI and displaying an image of the ROI from the energy discriminating CT data wherein portions of the image are weighted differently based on material composition.

The present invention also includes a computer readable storage medium is disclosed having a computer program stored thereon and representing a set of instructions that when executed by a computer causes the computer to identify material characteristics of an ROI from energy discriminating CT data acquired from the ROI. The computer is also caused to weight the energy discriminating CT data associated with particular regions of the ROI based on the material characteristics identified in those regions and reconstruct an image of the ROI from the weighted energy discriminating CT data.

The present invention has been described in terms of the preferred embodiment, and it is recognized that equivalents, alternatives, and modifications, aside from those expressly stated, are possible and within the scope of the appending claims.

What is claimed is:

1. An imaging system comprising:
   a radiation source configured to project radiation toward an object to be scanned;
   an energy discriminating detector assembly having a plurality of detector elements and configured to detect radiation emitted by the radiation source and attenuated by the object to be scanned; and
   a computer programmed to:
   count a number of photons detected by each detector element and associate an energy value to each counted photon;
   determine a material composition of a CT view from the number of photons counted and the energy value associated with each counted photon;
   apply a weighting to the CT view based on the material composition of the CT view; and
   reconstruct an image with differential weighting based on the weighting of the CT view.

2. The system of claim 1 wherein each detector element is further configured to acquire attenuation data from a respective voxel within a volume of interest (VOI).

3. The system of claim 2 wherein the computer is further programmed to determine at least one of atomic number and density for the material composition in each voxel from the number of photons counted and energy value associated with each counted photon.

4. The system of claim 3 wherein the computer is further programmed to weight a given voxel as a function of the at least one of atomic number and density of the material composition for the given voxel.

5. The system of claim 2 wherein the computer is further programmed to segment the attenuation data from each voxel based on whether that imaged in each voxel corresponds to a targeted material or a non-targeted material.

6. The system of claim 5 wherein the computer is further programmed to weight the attenuation data from a given voxel corresponding to the non-target material to have a magnitude equal to attenuation data corresponding to a background noise level of the system.

7. The system of claim 5 wherein the computer is further programmed to weight each CT view based on a position of a corresponding voxel in the VOI.

8. The system of claim 1 wherein the computer is further programmed to apply a pre-determined weighting to each CT view based on a believed anatomical composition of the VOI.

9. The system of claim 1 wherein the computer is further programmed to weight attenuation data acquired by detector elements impinged with low intensity radiation more heavily than attenuation data acquired by detector elements impinged with high intensity radiation for materials determined to have a high atomic number.

10. The system of claim 9 wherein the computer is further programmed to uniformly weight attenuation data corresponding to materials determined to have a low atomic number.

11. The system of claim 1 wherein the computer is further programmed to apply a plurality of weightings to dissimilarly weight different material compositions of the VOI.

12. The system of claim 1 wherein the computer is further programmed to decompose attenuation data output by the detector assembly into at least two data sets, wherein each data set is associated with a selected basis material.

13. The system of claim 12 wherein the computer is further programmed to determine a line integral density for each of the data sets.

14. The system of claim 13 wherein the computer is further programmed to select a mass attenuation coefficient to correspond to each data set based on the selected basis material associated with each data set.

15. The system of claim 14 wherein the computer is further programmed to weight the line integral density of each data set by the corresponding selected mass attenuation coefficient.

16. The system of claim 15 wherein the computer is further programmed to sum weighted line integral densities to form a modified projection for image reconstruction.

17. The system of claim 16 wherein the computer is further programmed to reconstruct an image from the modified projection and wherein the image is absent of beam hardening artifacts.

18. The system of claim 12 wherein the selected basis materials associated with the data sets are water and bone.

19. The system of claim 12 wherein the selected basis materials associated with the data sets are water and iodine.

20. The system of claim 1 wherein the computer is further programmed to assign a color to the weighting to visually differentiate that imaged in the CT view from that imaged in another CT view upon image reconstruction.

21. A method of radiographic imaging comprising the steps of:
acquiring energy discriminating CT data from an ROI, wherein the acquisition of energy discriminating CT data comprises counting a number of detected photons:
associating each of the photons with a plurality of energy bins;
determining a material composition breakdown of the ROI from the energy discriminating CT data and based on a photon occupancy of the energy bins;
applying one or more weightings to the energy discriminating data based on the material composition of the ROI; and
displaying an image of the ROI from the energy discriminating CT data wherein portions of the image are weighted differently based on material composition.

22. The method of claim 21 further comprising the step of acquiring x-ray attenuation data from the ROI in addition to the energy discriminating CT data.

23. The method of claim 21 further comprising the step of isolating energy discriminating CT data corresponding to targeted materials within the ROI from energy discriminating CT data corresponding to non-targeted materials within the ROI and weighting the energy discriminating CT data as a function of attenuation differences between the energy discriminating CT data corresponding to targeted materials and the energy discriminating CT data corresponding to non-targeted materials.

24. The method of claim 23 further comprising the step of weighting the energy discriminating CT data corresponding to non-targeted materials within the ROI similarly to data corresponding to a background noise level.

25. The method of claim 21 further comprising the step of determining an atomic number for a given material in the ROI from the energy discriminating CT data and determining a degree of weighting for the material from the atomic number of the given material.

26. The method of claim 21 further comprising the step of pre-selecting a weighting function to be applied to the energy discriminating CT data prior to displaying the image based on a known anatomical composition of the ROI.

27. The method of claim 21 further comprising the step of applying multiple weighting functions to the energy discriminating CT data to dissimilarly weight different materials in the ROI.

28. The method of claim 27 further comprising the step of displaying a single composite image of dissimilarly weighted materials.

29. The method of claim 21 further comprising the step of applying a first weighting to the energy discriminating CT data acquired from low energy x-rays passing through materials with high atomic number and a second weighting to CT data acquired from x-rays passing through materials with low atomic number.

30. The method of claim 21 further comprising the step of color-coding portions of the image to differentiate one material from another in the image.

31. The method of claim 21 further comprising the step of extracting density information for a material in the ROI from the energy discriminating CT data.

32. The method of claim 31 further comprising the step of assigning a color to a given pixel in the image as a fraction of the density information for the material imaged in the given pixel.

33. The method of claim 32 further comprising the step of adjusting an intensity of the given pixel to reflect an attenuation of the energy discriminating CT data utilized to reconstruct the given pixel.

34. The method of claim 31 further comprising the step of providing a color mapping of the ROI as a function of variations in the density information for materials of which the ROI is composed.

35. The method of claim 21 further comprising the step of adaptively selecting at least one weighting fraction to be applied to the energy discriminating CT data from a plurality of weighting fractions that may be applied based on the material composition of the ROI.

36. The method of claim 21 further comprising the step of decomposing the energy discriminating CT data into at least two data sets, each data set corresponding to a specific material within the ROI.

37. The method of claim 36 further comprising the step of determining a line integral density for each of the data sets.

38. The method of claim 37 further comprising the step of determining a mass attenuation coefficient for each data set based on the respective material associated with each data set.

39. The method of claim 37 further comprising the step of modifying the line integral density of each data set by a respective mass attenuation coefficient.

40. The method of claim 39 further comprising the step of adding the modified line integral densities to one another to form a modified projection.

41. The method of claim 40 further comprising the step of reconstructing an image from the modified projection and wherein the image is absent of beam hardening artifacts.

42. The method of claim 40 further comprising the step of determining a CT number for a material in the ROI that is independent of a location of the material within the ROI from the energy discriminating CT data and attenuation data for the material.

43. The method of claim 36 wherein the data sets include a first data set comprised of energy discriminating CT data of bone in the ROI and a second data set comprised of energy discriminating CT data of iodine in the ROI.

44. The method of claim 36 wherein the data sets include a first data set comprised of energy discriminating CT data of fat in the ROI and a second data set comprised of energy discriminating CT data of aluminum in the ROI.

45. A computer readable storage medium having a computer program stored thereon and representing a set of instructions that when executed by a computer causes the computer to:
identify material characteristics of an ROI from energy discriminating CT data acquired from the ROI, the energy discriminating CT data comprising photon count data of a number of photons and comprising photon energy data corresponding to the number of photons;
weight the energy discriminating CT data associated with particular regions of the ROI based on the material characteristics identified in those regions; and
reconstruct an image of the ROI from the weighted energy discriminating CT data.

46. The computer readable storage medium of claim 45 wherein the computer is further caused to determine an atomic number associated with a portion of the ROI based on the energy discriminating CT data associated with the portion.

47. The computer readable storage medium of claim 46 wherein the computer is further caused to identify targeted materials associated with the portion of the ROI based on the atomic number and isolate the energy discriminating CT data corresponding to the targeted material from energy discriminating CT data corresponding to non-targeted material.

48. The computer readable storage medium of claim 47 wherein the computer is further caused to weight the energy discriminating CT data corresponding to non-targeted material characteristics within the ROI equivalent to a background level.

49. The computer readable storage medium of claim 45 wherein the computer is further caused to apply a pre-selected weighting function to the energy discriminating CT data based on a believed anatomical composition of the ROI.

50. The computer readable storage medium of claim 45 wherein the computer is further caused to apply multiple weighting functions to the energy discriminating CT data to dissimilarly weight the energy discriminating CT data corresponding to various material characteristics in the ROI, and to display a single composite image therefrom.

51. The computer readable storage medium of claim 45 wherein the computer is further caused to determine atomic numbers corresponding to the material characteristics of the ROI and weight the energy discriminating CT data based on the determined atomic numbers.

52. The computer readable storage medium of claim 51 wherein the computer is further caused to non-uniformly weight energy discriminating CT data generated from low energy x-rays passing through materials determined to have a relatively high atomic number and uniformly weight energy discriminating CT data generated from x-rays passing through materials determined to have a relatively low atomic number.

53. The computer readable storage medium of claim 45 wherein the computer is further caused to color code the image to differentiate materials present in the ROI from one another.

54. The computer readable storage medium of claim 45 wherein the computer is further caused to extract density information from the energy discriminating CT data based on the material characteristics of the ROI.

55. The computer readable storage medium of claim 45 wherein the computer is further caused to display the reconstructed image in color to display density information of the ROI.

56. The computer readable storage medium of claim 45 wherein the computer is further caused to generate a color mapping of the ROI as a function of density variations in the ROI.

57. The computer readable storage medium of claim 45 wherein the computer is further caused to display intensity variations within the reconstructed image to illustrate attenuation variations in the ROI.

58. The computer readable storage medium of claim 45 wherein the computer is further caused to adaptively select at least one weighting function from a plurality of weighting functions based on identified material characteristics of the ROI to weight the energy discriminating CT data.

59. The computer readable storage medium of claim 45 wherein the computer is further caused to compare the identified material characteristics to a reference material and decompose the energy discriminating CT data into at least one of a plurality of predefined bins based on the comparison.

60. The computer readable storage medium of claim 59 wherein the computer is further caused to determine line integral densities of the reference material across the ROI.

* * * * *

UNITED STATES PATENT AND TRADEMARK OFFICE
CERTIFICATE OF CORRECTION

PATENT NO. : 7,583,779 B2
APPLICATION NO. : 10/904716
DATED : September 1, 2009
INVENTOR(S) : Tkaczyk et al.

It is certified that error appears in the above-identified patent and that said Letters Patent is hereby corrected as shown below:

Col. 18, line 5, delete "fraction" and substitute therefore -- function --;
      line 17, delete "fraction" and substitute therefore -- function --; and
      line 19, delete "fractions" and substitute therefore -- functions --.

Signed and Sealed this

Twenty-seventh Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,583,779 B2 Page 1 of 1
APPLICATION NO. : 10/904716
DATED : September 1, 2009
INVENTOR(S) : Tkaczyk et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 789 days.

Signed and Sealed this

Fourteenth Day of September, 2010

David J. Kappos
*Director of the United States Patent and Trademark Office*